(12) United States Patent
Bartsch et al.

(10) Patent No.: US 8,165,382 B2
(45) Date of Patent: Apr. 24, 2012

(54) GLAZING INSPECTION METHOD

(75) Inventors: Ingo Bartsch, Dorsten (DE); Simon Peter Aldred, Tarleton (GB)

(73) Assignees: Pilkington Group Limited, St. Helens, Merseyside (GB); Pilkington Automotive Deutschland GmbH, Witten (DE)

(*) Notice: Subject to any disclaimer, the term of this patent is extended or adjusted under 35 U.S.C. 154(b) by 535 days.

(21) Appl. No.: 12/301,787

(22) PCT Filed: May 22, 2007

(86) PCT No.: PCT/GB2007/050282
§ 371 (c)(1),
(2), (4) Date: Nov. 21, 2008

(87) PCT Pub. No.: WO2007/135465
PCT Pub. Date: Nov. 29, 2007

(65) Prior Publication Data
US 2010/0232677 A1 Sep. 16, 2010

(30) Foreign Application Priority Data
May 23, 2006 (GB) .................................. 0610148.9

(51) Int. Cl.
G06K 9/00 (2006.01)
(52) U.S. Cl. ...................... 382/141; 356/239.1; 356/600; 356/237.1; 382/140; 382/106; 382/270
(58) Field of Classification Search ............... 356/239.1, 356/237.2, 600, 237.1; 382/140–152, 103, 382/106–107, 270–274
See application file for complete search history.

(56) References Cited

U.S. PATENT DOCUMENTS
4,249,823 A 2/1981 Task
(Continued)

FOREIGN PATENT DOCUMENTS
DE 2310763 A 9/1974
(Continued)

OTHER PUBLICATIONS
"Standard Test Method for Measuring Angular Displacement of Multiple Images in Transparent Parts," *ASTM Standard*, 1998, pp. 1-4, F-1165, ASTM International, West Conshohocken, PA.
(Continued)

*Primary Examiner* — Gregory J Toatley
*Assistant Examiner* — Iyabo S Alli
(74) *Attorney, Agent, or Firm* — Buchanan Ingersoll & Rooney PC

(57) ABSTRACT

Methods of determining the divergence angle between a primary image and a secondary image generated by a glazing are disclosed. In a first method, a glazing is illuminated with a light source and a primary and a secondary image of the light source, generated by the glazing, are captured using an image capture device. The distance between the primary and the secondary image is determined, and the divergence angle determined from this distance. In a second method, the primary and secondary images are viewed on a target marked with a scale indicating the divergence angle. The divergence angle is read from the scale and the positions the primary and secondary image. In this second method, the light source is located at the center of the target. In both methods, the light source comprises at least one light emitting diode. Preferably, the method is used to examine the edge region of a glazing.

23 Claims, 9 Drawing Sheets

U.S. PATENT DOCUMENTS

| | | |
|---|---|---|
| 4,461,570 A | 7/1984 | Task et al. |
| 4,776,692 A | 10/1988 | Kalawsky |
| 4,837,449 A | 6/1989 | Maltby, Jr. |
| 5,146,282 A | 9/1992 | Guering et al. |
| 5,343,288 A | 8/1994 | Cohen et al. |
| 5,446,536 A * | 8/1995 | Miyake et al. ............. 356/239.1 |
| 5,621,520 A | 4/1997 | Hoffman |
| 5,726,749 A | 3/1998 | Schave |
| 2002/0154298 A1 | 10/2002 | Hagen et al. |
| 2007/0035733 A1 | 2/2007 | Reich et al. |
| 2008/0225115 A1* | 9/2008 | Matsushita ................... 348/129 |
| 2010/0232677 A1 | 9/2010 | Bartsch et al. |

FOREIGN PATENT DOCUMENTS

| | | |
|---|---|---|
| FR | 2 846 096 A1 | 4/2004 |
| WO | WO 2004/088294 A1 | 10/2004 |
| WO | WO 2005/026660 A1 | 3/2005 |
| WO | WO 2007/135465 A3 | 11/2007 |

OTHER PUBLICATIONS

Office Action dated Aug. 4, 2010, issued by the Chinese Patent Office in corresponding Chinese Patent Application No. 200780023867.7 and English language translation of Office Action.

First Office Action issued on Mar. 16, 2009 by the European Patent Office in corresponding European Patent Application No. 07 733 703.8.

Second Office Action issued on May 20, 2010 by the European Patent Office in corresponding European Patent Application No. 07 733 703.8.

International Preliminary Report on Patentability (IPRP) (Form PCT/IB/373) and Written Opinion of the International Searching Authority and International Preliminary Report on Patentability (Form PCT/ISA/273) issued in corresponding International Application No. PCT/GB2007/050282 dated Nov. 27, 2008.

International Search Report (PCT/ISA/210).

Search Report under Section 17(5) re Claims 1-12, 21, 22, issued in GB0610148.9, Sep. 26, 2006, The Patent Office, Patents Directorate, South Wales, UK.

Search Report under Section 17(6) re Claims 15-20, 21, 22, issued in GB0610148.9, Jan. 25, 2007, The Patent Office, Patents Directorate, South Wales, UK.

Search Report under Section 17(6) re Claims 13-14, 21,22, issued in GB0610148.9, Jan. 25, 2007, the Patent Office, Patents Directorate, South Wales, UK.

* cited by examiner

GLAZING INSPECTION METHOD

The present invention relates to methods of glazing inspection, in particular, methods for the inspection of automotive glazings.

During production, glass used in automotive glazings is inspected for various defects that may affect the optical quality of the finished glazing product. For example, the glass may contain inclusions or faults, such as nickel sulphide inclusions or bubbles. Alternatively, the glass may have faults acquired through processing, for example, edge faults, brillantatura and shiners from the cutting and grinding processes used to cut the glass to size, and distortion, thickness and curvature variations from the firing and bending processes used to shape the glass.

One particular issue for glass used to make windscreens and backlights is where a double or secondary image is seen when viewing an object through the glass. The effect is caused by thickness variations within the glass, present in varying degrees, and due to the shape of the screen and possible shaping errors introduced during manufacture. FIG. 1 is a schematic illustration of how a secondary image arises with a wedge. An observer 10 views a distant object 11 through a windscreen 12. The windscreen 12 varies in thickness in the region through which the observer 10 is looking. The screen effectively acts as a localised wedge refracting light as it passes through the glass. At the inner glass/air interface some light is reflected towards the outer glass/air interface, from which in due course some light is reflected back towards the driver, who thus observes a much weaker secondary image displaced by an angle $\theta$ from the primary image. The angle $\theta$ indicates the divergence of the secondary image from the primary image of the object and is dependent of the amount of wedge or curvature in the glass at the point of viewing.

Excessive levels of secondary image are disconcerting for the driver of a vehicle in which the windscreen is fitted and also give rise to safety concerns. Under ECE R43, the amount of secondary image allowable within a windscreen is measured in terms of the divergence angle $\theta$ between the primary and the secondary image. The maximum acceptable divergence angle at present is 15 arc minutes.

Whether a glazing passes or fails the ECE R43 secondary image criteria can be assessed in two ways, using either a backlit "ring-and-dot" target or a collimator-telescope arrangement.

The "ring-and-dot" target test is shown schematically in FIGS. 2a and 2b. As shown in FIG. 2a, the test involves an observer 13 viewing a "ring-and-dot" target 14 positioned on a light box 15 (containing a suitable light source 16, such as a tungsten filament bulb) through a glazing test sample 17. The glazing 17 is placed at a distance 1, greater than 7 m away from the light box 15, placed on a stand (not shown) at a rake angle $\phi$ mimicking that at which it will be installed in a vehicle, typically 60°. The "ring-and-dot" target 14 is designed to give a simple yes or no result. As shown in FIG. 2b, the "ring-and-dot" target 14 comprises a spot 18, having a diameter of 12 mm, positioned in the centre of a ring 19, having a thickness of 3 mm. The distance D between the edge of the spot 18 and the nearest point on the inside 19 of the ring subtends an angle of 15 arc minutes at a point at a distance 1 from the observer 13. D is given by the formula:

$$D = 1 \cdot \tan(15')$$

If the secondary image of the central dot appears to touch the primary image of the outer ring or lies outside the primary image of the outer ring, the glazing fails the test.

The test has disadvantages. Firstly, it is only a qualitative measurement of secondary image. Although various regions of the glazing can be tested, it is difficult to visualise how the secondary image varies across the glazing or to create a profile of secondary image variations. Only a profile showing areas which pass or fail the test could be produced. Secondly, the perceived amount of secondary image observed may vary from observer to observer making it difficult to guarantee the reliability of the test.

FIGS. 3a and 3b show the set up of the collimator-telescope test schematically. This test is advantageous in comparison with the ring-and-dot target test, as it provides quantitative measurements of secondary image.

FIG. 3a is a schematic cross section of the set-up for the collimation test. A collimator 20 forms an image of a polar co-ordinate system, having a bright point at its centre (from a point light source 21), at infinity. In an observation telescope 22, a small opaque spot 23, having a diameter slightly greater than that of the projected bright point is placed on the optical axis at the focal plane. A sheet of glass 24 is placed between the collimation telescope 20 and the observation telescope 22. If the sheet of glass 24 exhibits secondary image, this will be detected with the observation telescope and quantified using a polar co-ordinate system.

FIG. 3b shows the polar co-ordinate system used to determine the angle between the primary and secondary images. Either a target in the observation telescope 22 or a grating in the collimation telescope 20 can be marked up with the co-ordinates. Major axes 25 are marked around the circle at intervals of 30°. Each axis is marked radially from the centre of the circle in arc minutes. These markings are not shown for clarity. If the sheet of glass 24 exhibits secondary image, a weak spot 27 appears at a certain distance from the centre of the polar co-ordinate system. This weak spot 27 is the secondary image of the light source 21. The dark spot 28 represents the centre of the field of vision, and is caused by the opaque spot 23 in the observation telescope. The purpose of the opaque spot is to block the bright primary image, which would otherwise interfere with the location of the weak secondary spot. The divergence angle (the degree of separation between the images) is then read in terms of arc minutes directly from the polar co-ordinate scale.

However, this method also has drawbacks. Although it gives a quantitative estimate of the degree of distortion of the glass, the system needs to be carefully aligned and positioned by hand for individual sheet of glass inspected. Again, an operator is needed to interpret the position of the secondary image to determine the divergence angle. In order to produce a profile, indicating the secondary image angle across the sheet of glass, many hundreds of measurements must be made by hand across the entire surface of the glass. This is time consuming and impractical. Also, the secondary spot can be very difficult to see because of its low intensity.

The present invention aims to address these problems by providing, in a first aspect, a method of determining the divergence angle between the primary image and secondary image generated by a glazing, comprising illuminating the glazing with a light source, capturing the primary and secondary image of the light source generated by the glazing using an image capture device, determining the distance between the primary and secondary image, and using the distance, calculating the divergence angle between the primary and secondary image.

By using an image capture device, and therefore automating part of the inspection process, it is possible to remove the uncertainties associated with using individual observers to measure a quantitative divergence angle for a particular glazing.

The glazing may be illuminated in transmission. Preferably, the image capture device is a CMOS (combined metal oxide semiconductor) camera. Alternatively, the image capture device may be a CCD (charge coupled device) camera. The light source is preferably an LED (light emitting diode) array. The array may comprise at least two LEDs. Preferably, the array comprises three LEDs. Preferably, a primary image and a secondary image are generated for each LED in the array. The LEDs in the array may be aligned along a line inclined at 45°.

Preferably, the light source is an LED array comprising three LEDs aligned along a line inclined at 45°.

Preferably, the divergence angle is determined in an edge region of the glazing.

In addition, the method may include the steps of calculating the divergence angle at a plurality of points on the glazing; and generating a divergence angle profile of the glazing.

The glazing may be a single ply of glass. Alternatively, the glazing may be a laminated glazing, comprising two plies of glass having an interlayer laminated therebetween.

The present invention also provides computer program, which when run on a computer causes the computer to perform the steps of capturing an image comprising plurality of objects generated by a glazing illuminated by a light source using an image capture device; duplicating the objects into first and second sets; for the first set: calculating series of local mean values of the objects' intensity; computing and applying a local intensity thresholds based on the mean values; maintaining a subset of the least intense objects; determining the centre positions and size of each of the objects in the subset; for the second set: applying a second series of local intensity thresholds; maintaining a subset of the most intense objects; determining the centre positions and size of each of the objects in each subset; performing a check to determine whether all of the objects in the first subset and the second subset are from the same light source; when all of the objects are from the same light source: sorting the objects in each subset by X and Y coordinate positions; combining corresponding pairs of objects from the first and second subset; determining the distance between each object in each corresponding pair; and calculating a divergence angle using the distance.

The check to determine whether all of the objects in the first subset and the second subset are from the same light source comprises the steps of determining the number of objects in the first subset; determining the number of objects in the second subset; calculating the gradient of a line joining the objects in the first subset; rejecting objects in the second subset falling on a line having a different gradient; and re-determining the number of objects in the second subset.

The present invention also provides, in a second aspect, a method of determining a divergence angle between a primary and a secondary image generated by a glazing, comprising illuminating the glazing with a light source, viewing the primary and secondary image of the light source generated by the glazing on a target, the target being marked with a scale indicating the divergence angle between the primary and a secondary image, and determining the divergence angle from the scale on the target and the positions of the primary and the secondary image, wherein the light source is located at the centre of the target.

By using a target having a marked scale and a light source at the centre, it is possible to provide a simple, quantitative measure of the divergence angle, without the need for the precise optical alignments of the prior art.

Preferably, the target is circular, and the scale comprises a series of concentric rings. More preferably, the concentric rings are at intervals of 2 arcmin. The light source may be a light emitting diode.

The glazing may be a single ply of glass. Alternatively, the glazing may be a laminated glazing, comprising two plies of glass having an interlayer laminated therebetween.

Preferably, the glazing inspected is an automotive glazing. More preferably, the glazing is a windscreen or a backlight.

The present invention will now be described by way of example only, and with reference to the accompanying drawings in which:

FIG. 1, referred to above, is a schematic representation of the generation of secondary images;

FIG. 2a, referred to above, is a schematic cross section of the test set up for a target test;

FIG. 2b, referred to above, is a schematic front view of a target;

FIG. 3a, referred to above, is a schematic cross section of the test set up for a collimation test;

FIG. 3b, referred to above, illustrates the polar co-ordinate system used in the collimation test;

One solution to the problem of ensuring accurate and reliable measurement of secondary images, especially those in the edge region of a glazing, is to provide a quantitative measurement system where the acquisition and processing of data is automated. This is the approach taken in a first aspect the present invention.

Figure 4:
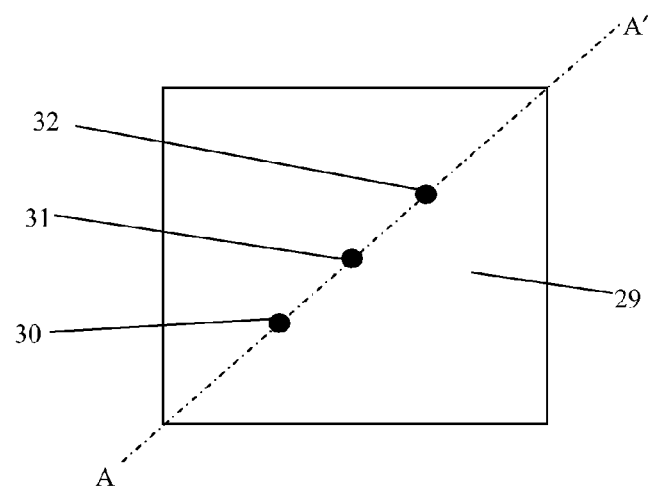
FIG. 4 is a schematic illustration of an LED array and target used in a first secondary image measurement system.

FIG. 4 shows a target 29 for use with a quantitative secondary image measurement system. An array of three light emitting diodes (LEDs) 30, 31, 32 are positioned 60 min apart along a line A-A' inclined at 45° on a target 29, 250 mm by 250 mm in size. The LEDs in this example emit green light at a power of 3 W. LEDs are extremely useful as a light source in optical measurement systems as they provide a bright, almost point source of light. The use of an array of three LEDs inclined at an angle is advantageous for taking measurements close to the edge of a glazing.

Figure 5:
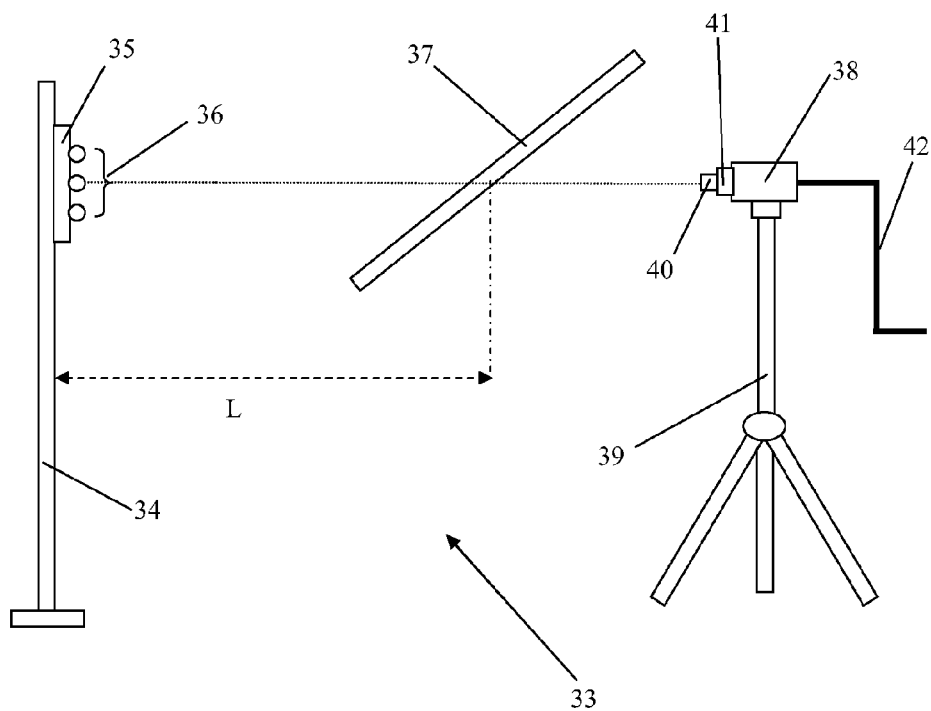
FIG. 5 is a schematic illustration of the set up of the first secondary image measurement system.

FIG. 5 shows the experimental set up for a first secondary image measurement system. The system 33 comprises a stand 34 on which the target 35 and LED array 36 are mounted. The stand 34 is positioned a distance L from a glazing 37. Preferably, L=7.5 m. A CMOS (complementary metal oxide semiconductor) camera 38, (available as the A601f-HDR from Basler AG, An der Strusbek 60-62, D-22926, Ahrensburg, Germany) is mounted on a tripod 39. A c-mount, f=100 mm lens 40 is used to image the LED array 36 onto the CMOS camera 38. A linear polarizer 41 is mounted between the lens 40 and the CMOS camera 38 to reduce the contrast between the primary and secondary images of the LED array 36, by suppressing the non-reflected component of the incident light. The CMOS camera 38 is connected to a computer (not shown) via a FireWire™ connection 42. The computer runs a real-time image capture program, for example, through LabView™, and a processing algorithm, discussed below.

The CMOS camera 38 has a plurality of pixels, each of which comprises a photodiode that converts light to electric charge, a charge-to-voltage converter, a reset and select transistor and an amplifier. Timing and read out signals and an array of column output signal interconnects are provided by a metal grid that overlays the entire sensor. Multiplexing electronics are arranged in a column outside the pixel array and connected to the column lines. The signals in the array are read out using X-Y addressing.

Figure 6:
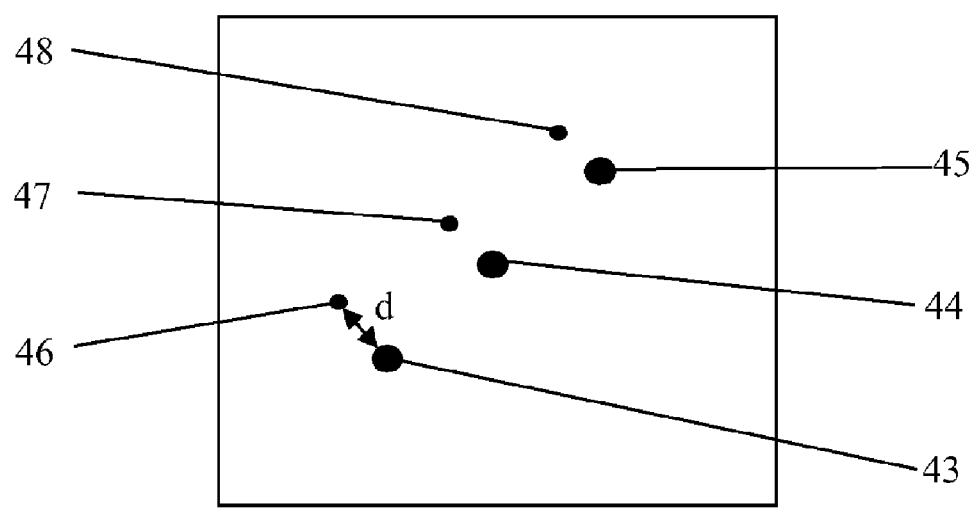
FIG. 6 is a schematic illustration of the view of the camera in FIG. 5.

The image captured by the CMOS camera 38 is shown in FIG. 6. Three bright spots 43, 44, 45 are seen, and are the primary images of the LED array 36. Three fainter spots 46, 47, 48 are also seen, each at a constant deflection distance d from one of the nearest bright spot 43, 44, 45. These are the secondary images of the LED array 36, and each corresponds to one of the bright spots 43, 44, 45.

As the distance between the LEDs in the array 36 is known, it is possible to calibrate the camera pixels in mm/pixel, based on the distribution of the primary images. The mm/pixel value is then used to determine the deflection distance d of any of the secondary image spots from its corresponding bright spot in mm. The divergence angle, between the primary and secondary images is then calculated using the equation:

$$\theta = \arctan(d/L)$$

where both d and L are in mm. For the example discussed above, the divergence angle is equal to:

$$\theta = \arctan(d/7500)$$

To determine the divergence angle the secondary image measurement system must be able to locate the position of both bright, primary image spots, and fainter, secondary image spots. Detection of the fainter secondary image dots may become difficult under certain lighting conditions, for example, if there is too much residual light in the room where measurements are carried out, and/or if the measurement system is not set up properly. It is also possible for the CMOS camera 38 to detect faint spots from other light sources within the room. Therefore, one of the main tasks of the system is to differentiate between "real" spots, generated by the LED array 36, and "false" spots, generated by other light sources.

The system comprises a computer which runs an algorithm to identify objects in the image, which are the bright spots and darks spots, and calculate the divergence angle.

Bright spots can be found simply by applying a fixed threshold to the camera image and selecting the three largest spots. Faint secondary spots are more difficult to detect reliably due to possible variations in lighting conditions. A semi-automatic thresholding technique, in which the mean grey value of the image is combined with a user-defined threshold, may be used. In this manner, the system can be easily adapted to working under different lighting conditions. Only the three smallest spots from the thresholded image are selected and retained for further processing. The algorithm used also carries out a plausibility check to determine whether the selected spots are suitable for performing divergence angle calculations. However, it is preferable to use a system of local thresholds, where for every local area, a mean value of illumination is calculated, and a threshold value relative to this mean value is applied, as described below.

Figure 7:
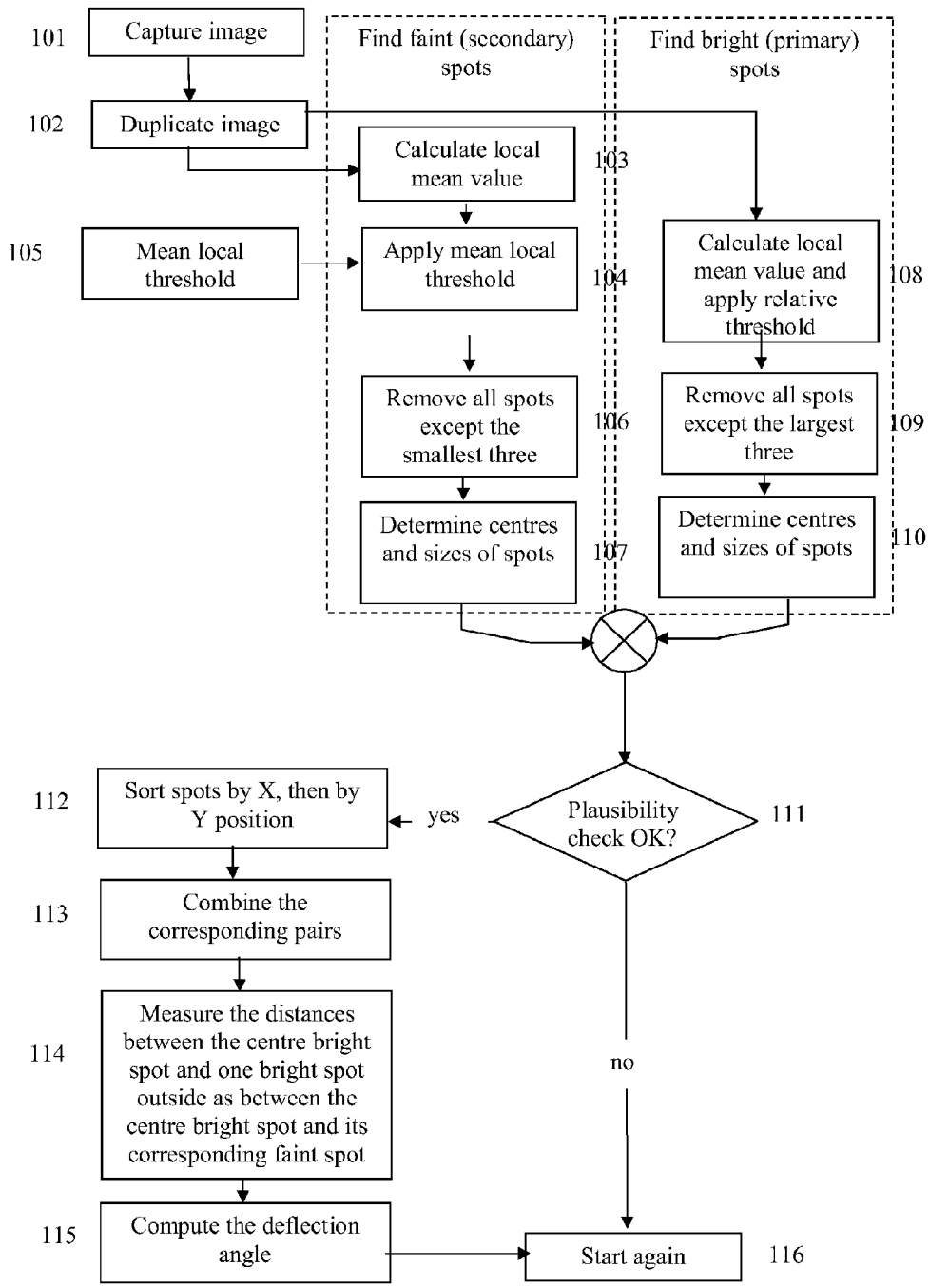
FIG. 7 is a flow chart of a calculation algorithm used in the first secondary image measurement system.

FIG. 7 is a flow chart illustrating the calculation algorithm. At step 101, the image of the bright and dark spots is captured. At step 102, the image is duplicated for use in processing. Considering the process for determining the faint, secondary spots first, using the first image, at step 103, the mean value of the intensity of all the available pixels in a local area is calculated. This is done by calculating a first mean intensity value of all of the pixels within a small square area, in a first position, moving the square to a second position and calculating a second mean intensity value. At step 104, a local relative threshold 105 (for the intensity of the spots, based on the mean value) is calculated and applied for each square. At step 106, all of the spots except for the smallest three are removed. At step 107, the centre positions and sizes of the spots are determined. The process for determining the bright spots is carried out simultaneously, using a second image. At step 108, a local relative threshold is determined and applied. At step 109, all of the spots, except for the brightest, are removed. At step 110, the positions of the centres and the sizes of the spots are determined. The results from both processes are combined, and a plausibility check applied at step 111. This plausibility check is described in more detail in FIG. 8. If the answer to the plausibility check is "yes", the algorithm continues with step 112 to sort the spots by X and then Y co-ordinate positions. At step 113, corresponding pairs of faint (secondary) and bright (primary) spots are combined. At step 114, the distance between the central bright spot and an outer bright spot, as well as the distance between each bright spot and corresponding faint spot, is measured. At step 115, the divergence angle is calculated from the distances between the spots. Once this process has finished, the algorithm starts again, and returns to step 112. If the answer plausibility check at step 111 is "no", the algorithm starts again and returns to step 101.

Figure 8:
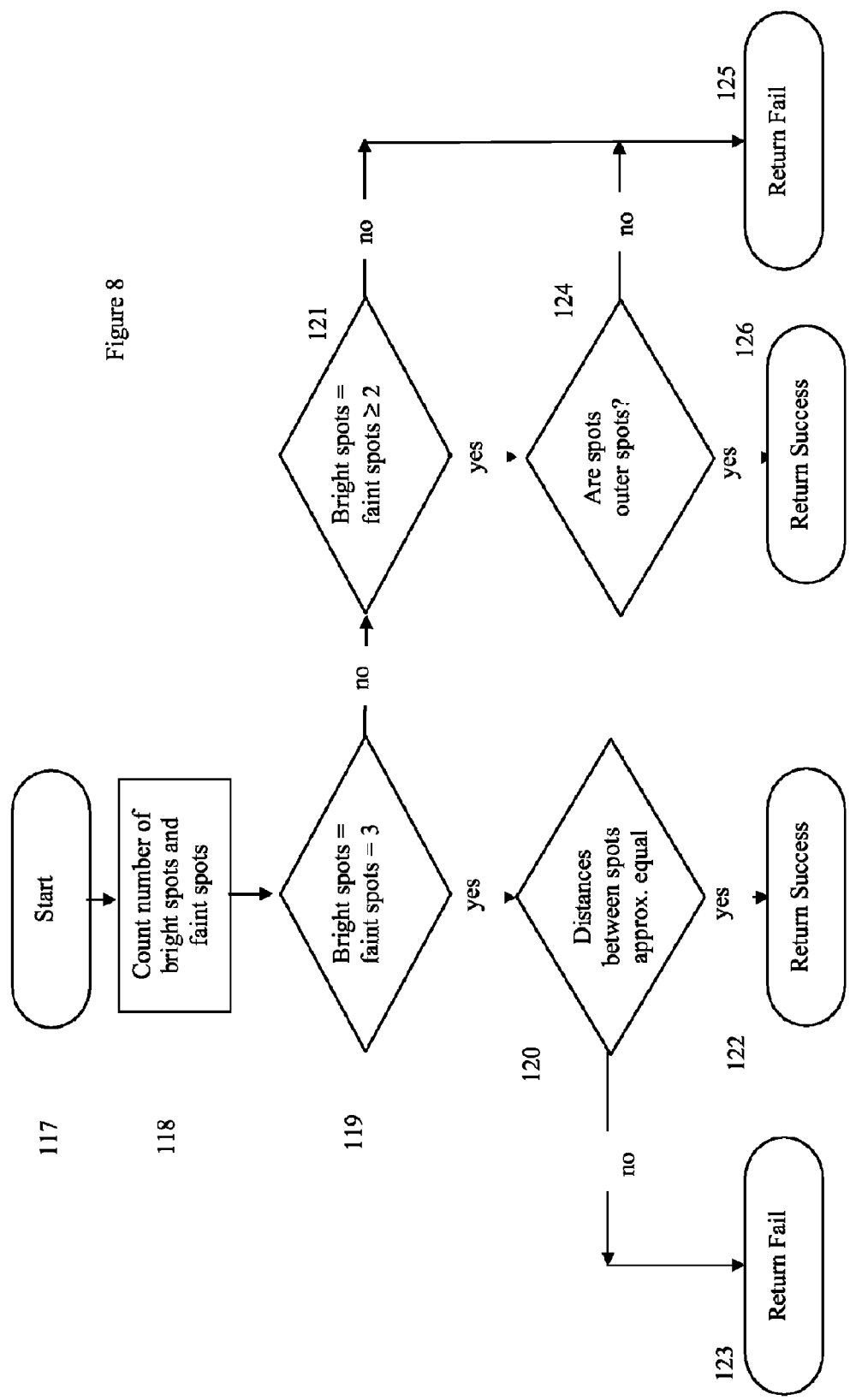
FIG. 8 is a flow chart of a plausibility check algorithm used in the first secondary image measurement system.

FIG. 8 is a flow chart illustrating the plausibility check. The algorithm starts at step 117. At step 118, the number of bright spots and faint spots are counted. At step 119, if the number of bright spots and the number of faint spots is three, the algorithm progresses to step 120. At step 120 if the distances between the bright spots and the distances between the faint spots are approximately equal, at step 122 a success is returned and the plausibility check 111 answers "yes". If the distances between the spots are different, at step 123 a fail is returned and the plausibility check 111 answers "no". However, if the answer at step 119 is no, at step 121 if the number of bright spots is at least two and the number of faint spots is at least two, the algorithm progresses to step 124. At step 124, the distance between the bright spots is calculated and compared with the distance between the faint spots to determine if two of the faint spots and two of the bright dots are actually the outer two spots of the three spot array. If the answer at step 124 is yes, then at step 126 a success is returned, and the plausibility check 111 answers "yes". If the answer at step 124 is no, then at step 125 a fail is returned and the plausibility check 111 says "no". If the answer at step 121 is no, then at step 125 a fail is returned and the plausibility check 111 answers "no".

Once the divergence angle has been calculated, it is output to an operator via a screen connected to the computer.

In order to determine the accuracy of the system, two tests were carried out to determine the accuracy of the system. Firstly, a series of optical reference wedges, available from Optical. Works Limited, Ealing Science Centre, Treloggan Lane, Newquay, Cornwall, TR7 1HX, UK, were used to determine the bias of the system. The reference wedges covered a range of 0 to 30 arcmin, with the secondary image generated by each wedge being measured by the system. Two sets of measurements were carried out, giving a root mean squared error of 0.4 arcmin and 0.3 arcmin respectively.

Secondly, the variation in results for different operators was examined. Six measurement zones, 40 mm×40 mm in size were defined on a windscreen. Four operators were asked to make three measurements per part, and the results recorded in Table 1 below. Each measurement is in arcmin.

TABLE 1

Secondary image measurements made by four operators and their range

| | \multicolumn{6}{c}{Sample Number} | | | | | |
|---|---|---|---|---|---|---|
| | 1 | 2 | 3 | 4 | 5 | 6 |
| Operator 1 | 13 | 9.8 | 7.1 | 7.6 | 9.6 | 12.9 |
| | 13.3 | 9.7 | 7.4 | 7.6 | 9.6 | 12.9 |
| | 13.1 | 9.2 | 7.2 | 7.6 | 9.5 | 13 |
| Range | 0.3 | 0.6 | 0.3 | 0 | 0.1 | 0.1 |
| Operator 2 | 13.3 | 9.7 | 7.4 | 7.7 | 9.9 | 12.9 |
| | 13.1 | 10 | 7.1 | 7.6 | 9.9 | 13 |
| | 12.9 | 9.8 | 7.1 | 8.1 | 9.9 | 12.8 |
| Range | 0.4 | 0.3 | 0.3 | 0.5 | 0 | 0.2 |
| Operator 3 | 13.3 | 10.2 | 7.1 | 8.2 | 10 | 12.9 |
| | 13.3 | 9.9 | 7.2 | 8 | 10 | 12.9 |
| | 12.9 | 10.2 | 7.4 | 8 | 10 | 12.9 |
| Range | 0.4 | 0.3 | 0.3 | 0.2 | 0 | 0 |
| Operator 4 | 12.9 | 9.3 | 7.3 | 7.9 | 9.6 | 13 |
| | 13.6 | 9.5 | 7.1 | 7.8 | 9.6 | 13 |
| | 13.5 | 9.5 | 7.3 | 7.9 | 9.8 | 12.9 |
| Range | 0.7 | 0.2 | 0.2 | 0.1 | 0.2 | 0.1 |

The estimated standard deviation $\sigma_e$ for repeatability, the variation in each operator's readings, is given by $$\sigma_e = \frac{R\_BAR}{d_2} = \frac{0.2575}{1.693} = 0.152$$

where R_BAR is the average of the range (where the range is the difference between the maximum and minimum readings for each operator on each given part) and $d_2$ is a constant, determined by the number of items in the sample, see for example "Business Statistics An Introductory Course", by Ken Black, ISBN0-314-92219-9.

The repeatability is given by $$\text{REPEATABILITY} = 5.15 \times \sigma_e = 0.78$$

where 5.15 is a constant, and represents 99% of the results for a normal distribution.

The reproducibility, or variation between operators, is determined by finding the overall average for each operator and then the range of operator averages, $R_0$, by subtracting the smallest average from the largest. From the numbers given above in Table 1, $$R_0 = 10.24 - 10.22 = 0.22$$

The estimated operator standard deviation is therefore:

$$\frac{R_0}{d_2^*} = \frac{0.22}{2.24} = 0.098$$

and the reproducibility $$5.15 \times \frac{R_0}{d_2^*} = 0.506$$

The adjusted reproducibility taking into account gauge variation is given by:

$$= \sqrt{\left[\left(\frac{R_0}{d_2^*}\right)^2 - \left(\frac{5.15 \times \sigma_e}{\sqrt{nr}}\right)^2\right]}$$

$$= \sqrt{\left[0.506^2 - \left(\frac{5.15 \times 0.152}{\sqrt{6 \times 3}}\right)^2\right]} = 0.47$$

where n is the number of parts and r the number of trials. The adjusted operator standard deviation is therefore $$\sigma_0 = \frac{0.47}{5.15} = 0.091$$

and the measurement system standard deviation, $\sigma_m$ is $$\sigma_m = \sqrt{\sigma_0^2 + \sigma_e^2} = 0.178$$

and the gauge system variation, is $$5.15 \times \sigma_m = 0.91.$$

The gauge system variation is therefore dominated by the instrument itself, and not by the operators. Therefore, unlike prior art systems, the accuracy of the divergence angle measured is virtually unaffected by the operator making the measurements.

Figure 9:
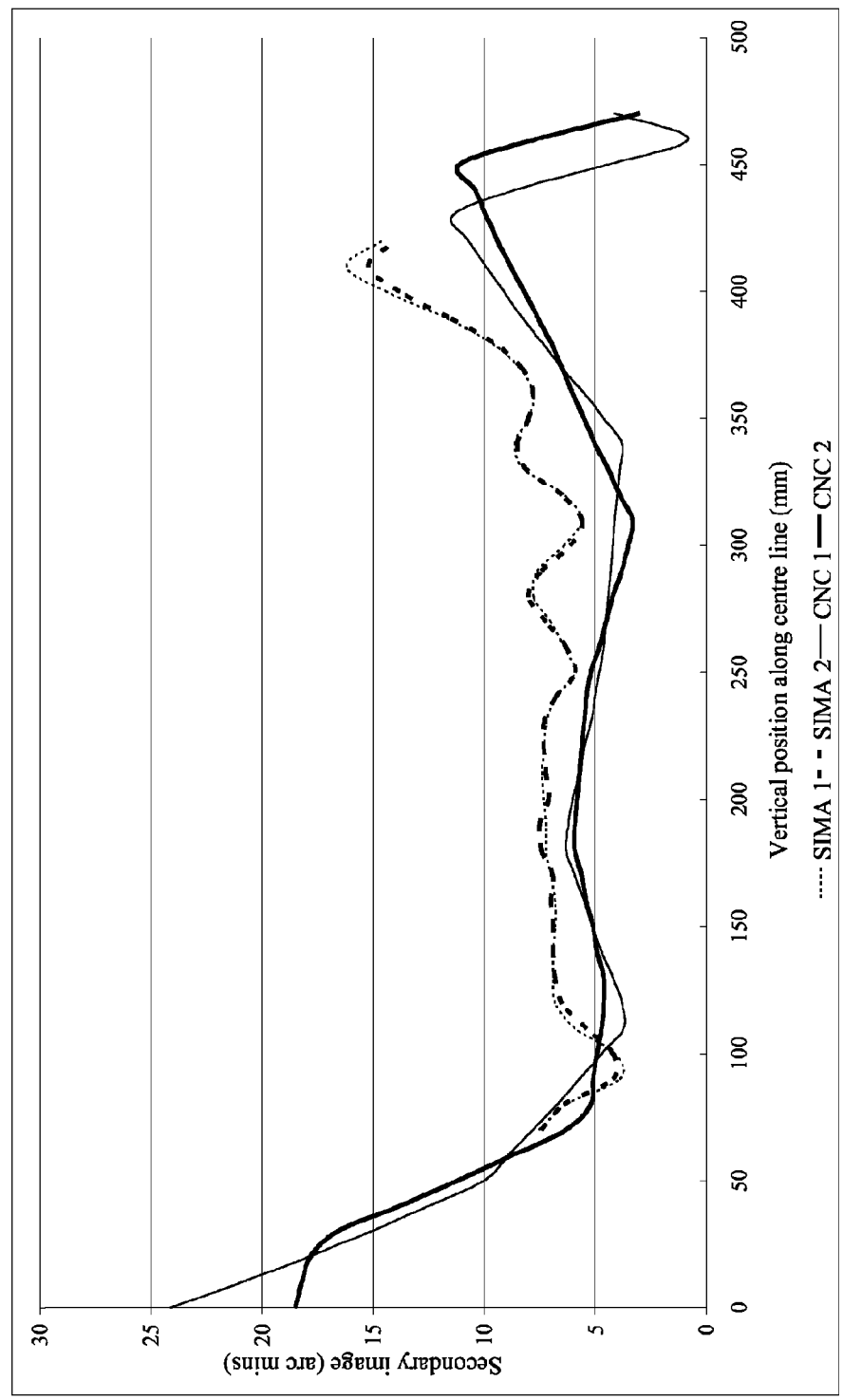
FIG. 9 is a chart showing a comparison of measured and calculated secondary image divergence angles for a windscreen.

Measurements taken using the secondary image measurement system of the first aspect of the present invention have also been compared with computer model predictions, based on CNC measurements. FIG. 9 is a chart showing how two measurements taken using the secondary image measurement system ("SIMA 1" and "SIMA 2") compare with two calculations ("CNC 1" and "CNC 2") made along a vertical axis of a windscreen. The x-axis scale is shown with 0 mm being the top of the windscreen. It can be seen that the measurements taken with the secondary image measurement system are repeatable and accurate, and agree in terms of magnitude with the model calculations based on CNC measurements. One possible cause of differences between the measurements and calculations is that the secondary image measurement system takes readings at much more closely-spaced points than the CNC measurement system. This results in some smoothing of secondary image data by the model, which is detected using the secondary image measurement system.

It is possible to use the system to provide a single measurement, or to take a series of measurements to produce a profile. Such a profile may be produced by taking measurements at a series of points across a glazing by repositioning the glazing and/or camera and target manually, or by automating the collection of data. Both single plies of glass, for example, toughened glass, and laminated glazings, typically comprising two plies of annealed glass having an interlayer laminated therebetween, may be inspected using the system. In laminated glazings, the divergence angle may arise as a result of variations in glass ply or laminate thickness.

Figure 10:
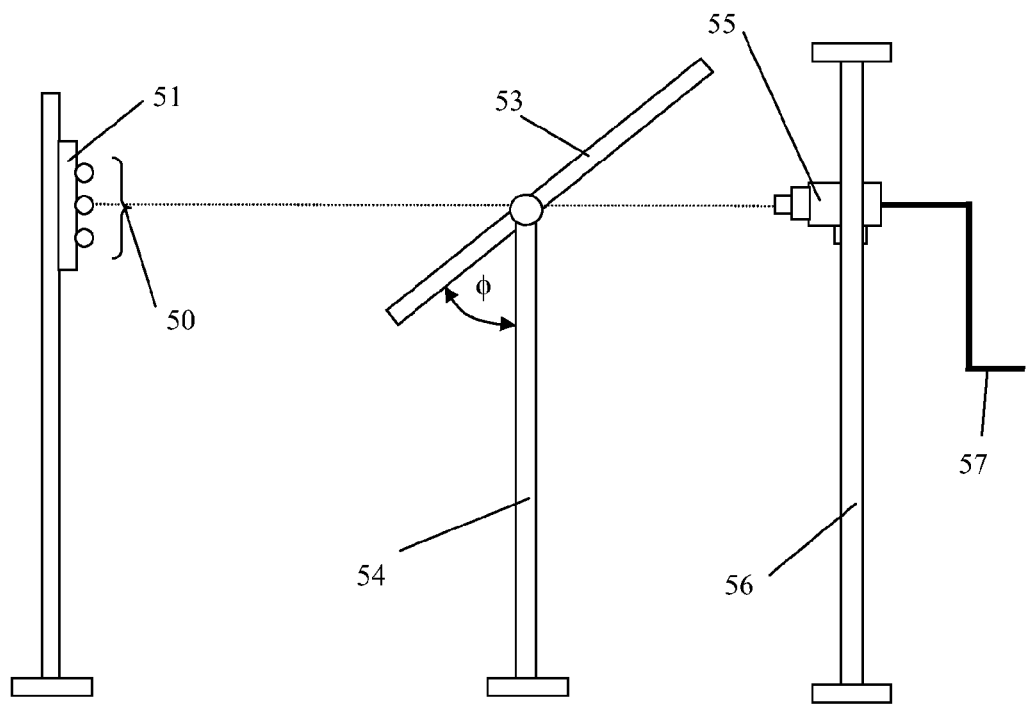
FIG. 10 is a schematic illustration of a set up for the automated collection of data using the first secondary image measurement system.

FIG. 10 is a schematic illustration of a secondary image measurement system for automatic collection of data. The system 49 comprises an LED array 50 mounted on a target 51 supported on a stand 52. A glazing 53 is mounted on a support stand 54, which allows its position to be varied in both the X and Y directions, and tilted through a rake angle φ. A CMOS camera 55 (having an associated lens and polariser, not shown) is mounted on a support stand 56. The support stand 56 allows the camera 55 to be moved in both X and Y directions. The camera 55 is connected to a computer (not shown) via a FireWire™ connection 57.

Figure 11:
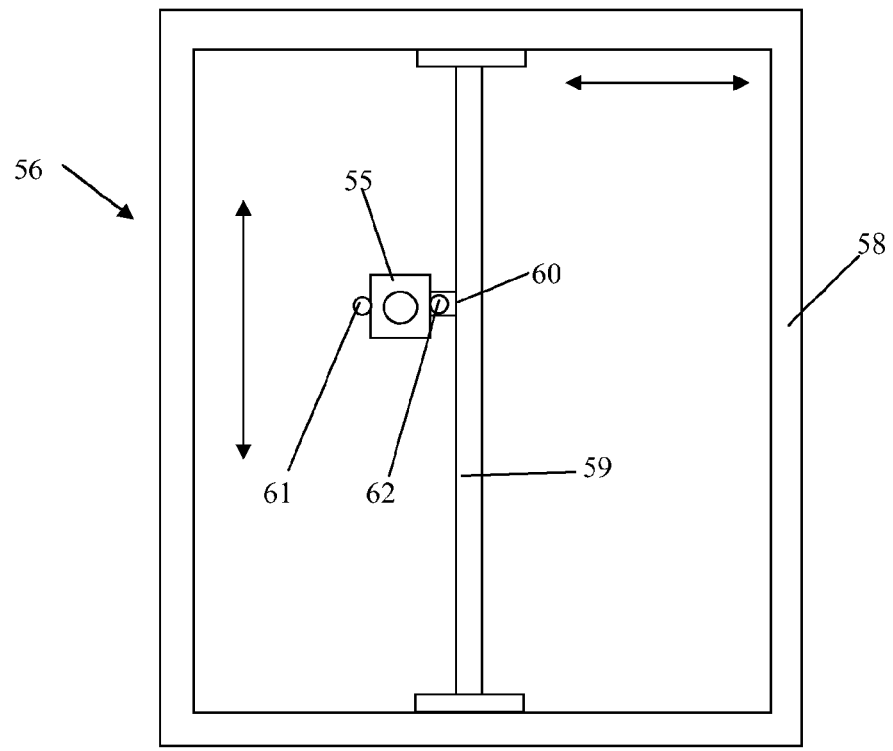
FIG. 11 is a schematic illustration of the camera support stand used in FIG. 10.

FIG. 11 is a front schematic view of the support stand 56. The support stand comprises an external frame 58 and a support member 59. The camera 55 is mounted on the support member by means of a ball and socket pivot 60. The pivot 60 enables the camera to be tilted to ensure accurate alignment between the camera 55, the glazing 53 and the LED array 50. Attached to the camera 55 are two laser pointers 61, 62. The laser pointers 61, 62 are used to identify the measurement point, and also to aid with the alignment of the camera 55. The support member 59 is in the form of a vertical slide, such that the camera 55 can be moved to any position on the member 59 and locked into place. The support member 59 is moveable from side to side on rails in the support frame 58, to allow raster scan measurements to be performed over the entire area of the glazing. A 2-D image of the glazing, with measurement points spaced approximately 100 mm apart takes less than 30 minutes to perform. The computer runs both the algorithm and allows the operator to position the camera. This positioning may be as the result of manually input commands or a program run by the computer.

Although in the above system, a target comprising three LEDs is used, the system is also able to work with a two LED target, and suitable adjustment to the various processing algorithms. In the above examples, a CMOS camera has been used as the image capture device. However, it is also possible to use a CCD (charge coupled device) camera as the image capture device.

This first secondary image measurement system offers many advantages over the prior art target and collimation tests. An accurate, quantitative measure of divergence angle can be obtained, as well as a full profile of the glazing being inspected. The measurement process may be automated. In addition, the positioning of the glazing may automated, for example, using a robot to position glazings on a support stand to be tested. This enables the system to be included in a production line.

Figure 1:
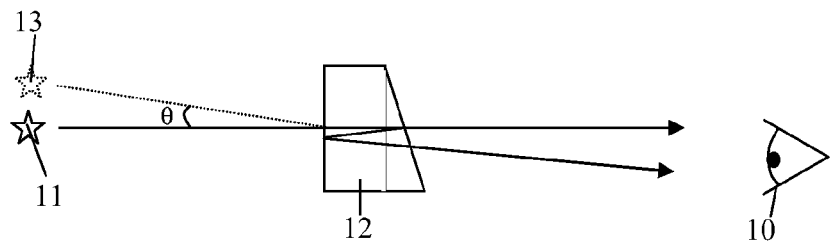
Figure 2A:
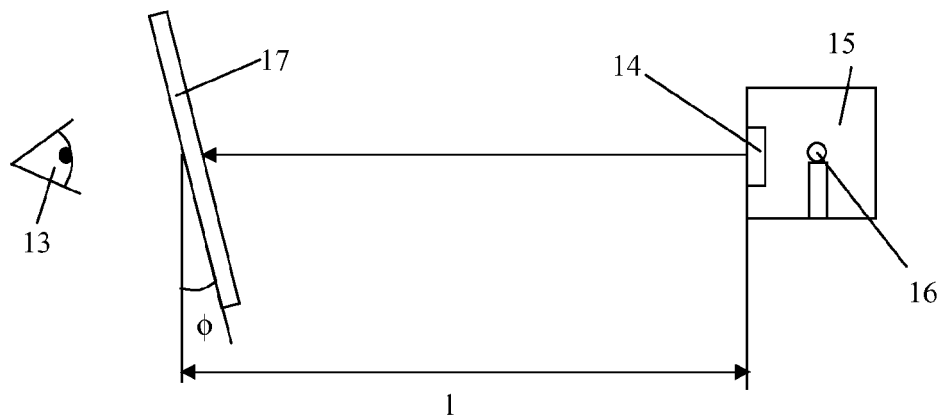
Figure 2B:
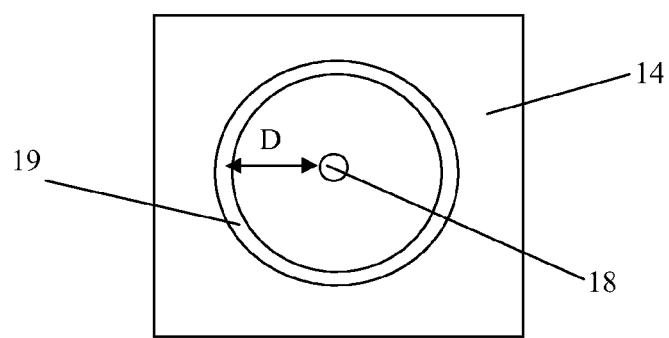
Figure 3A:
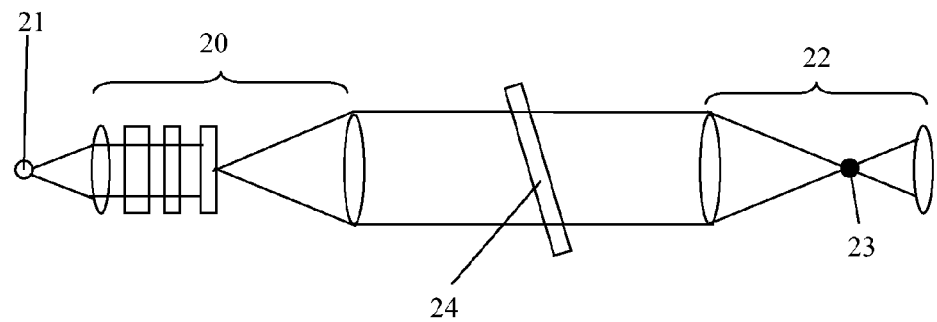
Figure 3B:
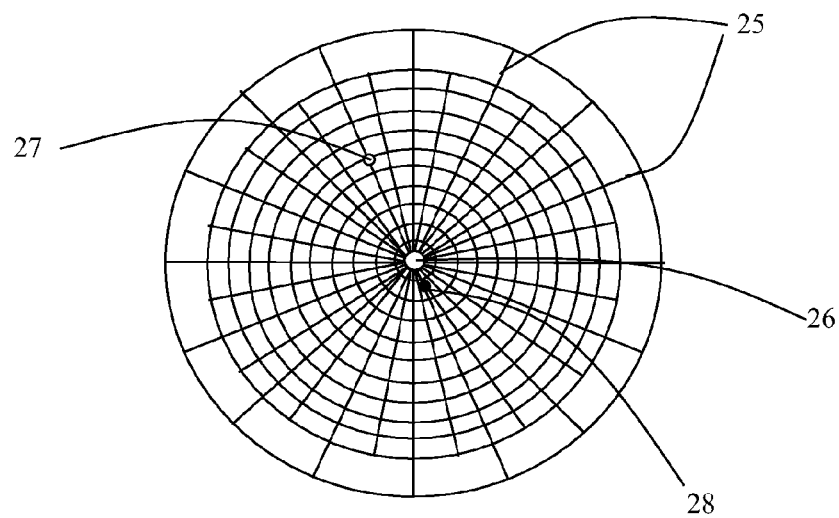
Figure 12:
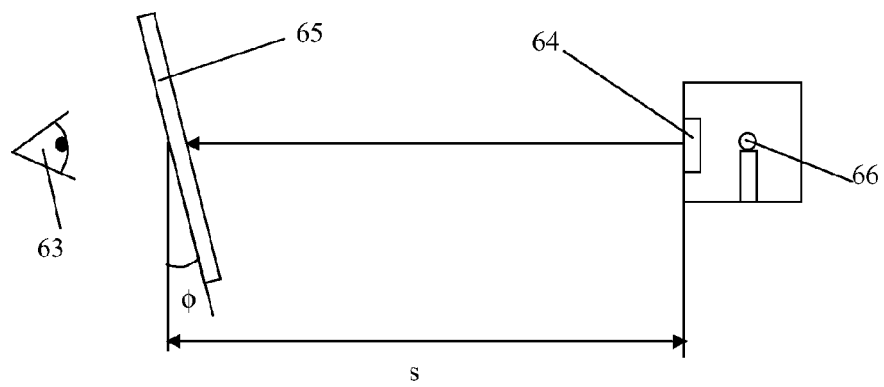
FIG. 12 is a schematic illustration of a second secondary image measurement system.
Figure 13:
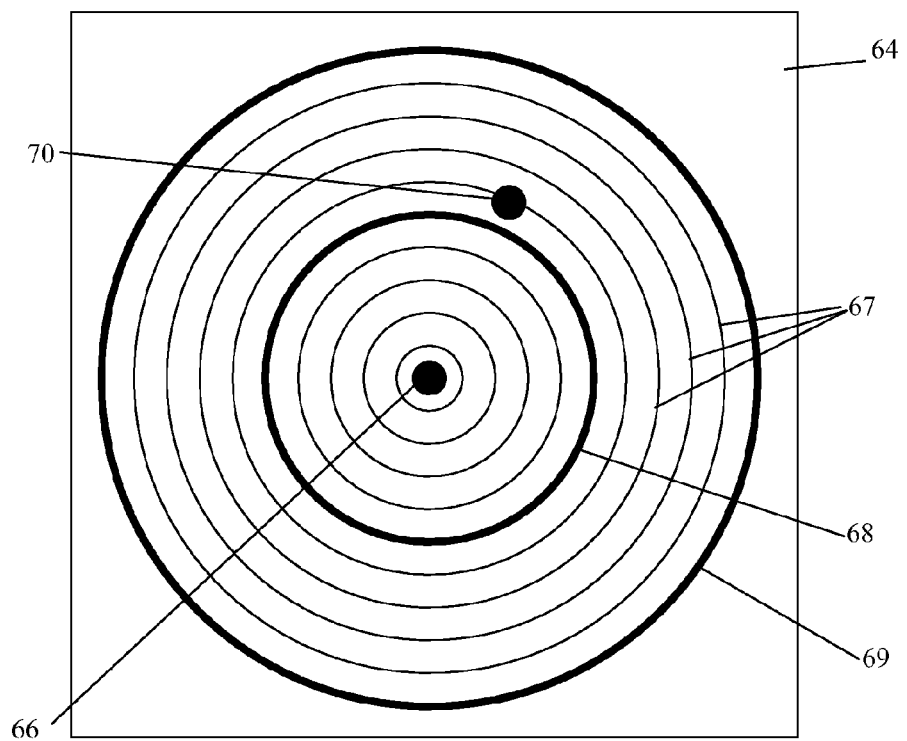
FIG. 13 is a schematic illustration of a target for use with the second secondary image measurement system.

A second aspect of the present invention provides a further solution to the problem of quantifying the divergence angle, in particular, in the edge region of a glazing, as shown in FIGS. 12 and 13. FIG. 12 shows the schematic set up of a second secondary image system. The overall set up is similar to that shown in FIG. 2a. An observer 63 views a target 64 through a glazing 65, set at a distance S away from the target 64. The target 64 is illuminated centrally by an LED 66, for example, a green LED. S is preferably more than or equal to 7 m. FIG. 13 shows the target for use in the second secondary image measurement system. The target 64 comprises a series of concentric rings 67, positioned at 2 arcmin intervals. The rings for 10 arcmin 68 and 20 arc min 69 are shown as a different colour. This may be achieved by colouring or illuminating the target appropriately. When viewed through a glazing in which distortion is present, a secondary image 70 of the LED 66 is seen, displaced over a number of rings 67 from the centre of the target 64. The divergence angle is determined by which ring 67 the secondary image 70 lies on or is closest to, leading to an accuracy of ±1 arcmin. The system may be used by an operator, for example, taking manual measurements through a pair of binoculars or other imaging device. This second secondary image measurement system has advantages over both the target test and collimation test, as it gives a simple, quantitative measurement of the divergence angle, without requiring a complex optical set up. The system may be used instead of or in tandem with the first secondary image measurement system described above, to screen glazings for further testing. Both single plies of glass, for example, toughened glass, and laminated glazings, typically comprising two plies of annealed glass having an interlayer laminated therebetween, may be inspected using the system. In laminated glazings, the divergence angle may arise as a result of variations in glass ply or laminate thickness.

Preferably, the glazings inspected using either or both systems are windscreens. However, the systems may be used to detect distortions and defects resulting in secondary image generation in other automotive glazings, such as backlights, sidelights and rooflights, or other glazings, such as architectural glazings.

The invention claimed is:

1. A method of determining the divergence angle between a primary image and a secondary image generated by a glazing, comprising:
   illuminating the glazing with a light source;
   capturing the primary image and the secondary image of the light source generated by the glazing using an image capture device;
   determining a distance between the primary image and the secondary image; and
   using the distance, calculating the divergence angle between the primary image and the secondary image.

2. The method of claim 1, wherein the glazing is illuminated in transmission.

3. The method of claim 1, wherein the image capture device is a CMOS (combined metal oxide semiconductor) camera.

4. The method of claim 1, wherein the image capture device is a CCD (charge coupled device) camera.

5. The method of claim 1, wherein the light source is an LED (light emitting diode) array.

6. The method of claim 5, wherein the array comprises at least two LEDs.

7. The method of claim 5, wherein the array comprises three LEDs.

8. The method of claim 6, wherein a primary image and a secondary image are generated for each LED in the array.

9. The method of claim 6, wherein the LEDs in the array are aligned along a line inclined at 45°.

10. The method of claim 1, wherein the light source is an LED array comprising three LEDs aligned along a line inclined at 45°.

11. The method of claim 1, wherein the divergence angle is determined in an edge region of the glazing.

12. The method according to, comprising the steps of:
    calculating the divergence angle at a plurality of points on the glazing; and
    generating a divergence angle profile of the glazing.

13. The method according to claim 1, wherein the glazing is a single ply of glass.

14. The method according to claim 1, wherein the glazing is a laminated glazing, comprising two plies of glass having an interlayer laminated therebetween.

15. A computer program, which when run on a computer causes the computer to perform the steps of:
    capturing an image comprising plurality of objects generated by a glazing illuminated by a light source using an image capture device;
    duplicating the objects into first and second sets;

for the first set:
  calculating a series of local mean values of the objects' intensity;
  computing and applying local intensity thresholds based on the mean values;
  maintaining a first subset of the least intense objects;
  determining the centre positions and size of each of the objects in the first subset;
for the second set:
  applying a second series of local mean intensity thresholds;
  maintaining a second subset of the most intense objects;
  determining the centre positions and size of each of the objects in the second subset;
performing a check to determine whether all of the objects in the first subset and the second subset are from the same light source;
when all of the objects are from the same light source:
sorting the objects in each subset by X and Y coordinate positions;
combining corresponding pairs of objects from the first subset and the second subset;
determining the distance between each object in each corresponding pair; and
calculating a divergence angle using the distance.

16. A method of determining a divergence angle between a primary and a secondary image generated by a glazing, comprising:
illuminating the glazing with a light source;
viewing the primary image and the secondary image of the light source generated by the glazing on a target, the target being marked with a scale indicating the divergence angle between the primary image and the secondary image; and
determining the divergence angle from the scale on the target and the positions of the primary image and the secondary image;
wherein the light source is located at the centre of the target.

17. The method of claim 16, wherein the target is circular, and the scale comprises a series of concentric rings.

18. The method of claim 17, wherein the concentric rings are at intervals of 2 arcmin.

19. The method of claim 16, wherein the light source is a light emitting diode.

20. A method according claim 16, wherein the glazing is a single ply of glass.

21. A method according to claim 16, wherein the glazing is a laminated glazing, comprising two plies of glass having an interlayer laminated therebetween.

22. The method of claim 1, wherein the glazing is an automotive glazing.

23. The method of claim 22 wherein the glazing is a windscreen or a backlight.

* * * * *